United States Patent [19]
Flinn

[11] Patent Number: 5,950,922
[45] Date of Patent: Sep. 14, 1999

[54] HOLDER FOR AN AIR FRESHENER

[76] Inventor: Gregory Flinn, 2764 NE. 34th St., Fort Lauderdale, Fla. 33306

[21] Appl. No.: 08/712,104

[22] Filed: Sep. 13, 1996

[51] Int. Cl.⁶ .................................. A61L 9/04; G09F 19/00
[52] U.S. Cl. .................................. 239/34; 239/44; 239/54; 239/56; 239/57; 40/768; 40/798
[58] Field of Search .................................. 239/44, 47, 54, 239/55, 56, 57, 145; 40/768, 769, 798, 799, 700, 124.11

[56] References Cited

U.S. PATENT DOCUMENTS

| | | | |
|---|---|---|---|
| 34,035 | 12/1861 | Dean | 40/769 |
| D. 269,902 | 7/1983 | Edwards . | |
| D. 366,107 | 1/1996 | Shaffer . | |
| 1,949,081 | 2/1934 | Overton | 40/700 X |
| 2,577,320 | 12/1951 | Fenyo . | |
| 2,579,715 | 12/1951 | Wilson et al. | 239/57 |
| 4,814,212 | 3/1989 | Spector . | |
| 4,883,692 | 11/1989 | Spector . | |
| 4,993,177 | 2/1991 | Hudson . | |
| 5,148,983 | 9/1992 | Muniz . | |
| 5,279,880 | 1/1994 | Cohart | 40/769 X |
| 5,304,358 | 4/1994 | Hoyt et al. | 239/56 X |
| 5,361,522 | 11/1994 | Green . | |
| 5,649,382 | 7/1997 | O'Keefe | 40/790 |

*Primary Examiner*—Andres Kashnikow
*Assistant Examiner*—Robin O. Evans
*Attorney, Agent, or Firm*—Herbert L. Lerner; Laurence A. Greenberg

[57] ABSTRACT

A holder for an air freshener comprising a wall section having a perimeter, a forward facing rim disposed along the perimeter, a rearward facing rim disposed along the perimeter forming a rear space for containing the air freshener. An image may be disposed on the forward facing surface of the wall section.

13 Claims, 2 Drawing Sheets

HOLDER FOR AN AIR FRESHENER

BACKGROUND OF THE INVENTION

1. Field of the Invention

The invention relates to a holder for an Air Freshener, and includes a wall section having a perimeter, a forward facing rim disposed along said perimeter, a rearward facing rim disposed along said perimeter forming a rear space for containing the air freshener, and wherein said forward facing rim defines a forward facing image area on said wall section.

2. Background and Prior Art

Air Fresheners are well known as devices or containers for containing aromatic or fragrant liquids or solids serving to dispel unpleasant odors or to infuse a given space with a pleasant fragrance. Commercially available air fresheners are usually formed as small can-shaped containers filled with the fragrant liquid, and having e.g. a wick inserted in the liquid to help disperse the fragrant vapors.

Such containers are typically unattractively looking and do not fit in the decor of spaces where people live, sleep or work.

The prior art includes U.S. Pat. No. 5,361,522, which shows an air freshener picture frame adapted to hold on its back side an air freshener, and holes in a picture area for admitting the fragrant vapors. U.S. Pat. No. 5,148,983 shows a scented souvenir card adapted to hold on its back side a scented carrier and having peripheral vents for admitting the fragrant vapors to the air. U.S. Pat. No. 4,883,692 shows an aromatic decorative figure or other object formed of foam plastic material having dispersed throughout its cellular structure a relatively large amount of volatile liquid fragrance.

The devices of the prior art suffer from the drawback that the holder or frame structure to a large extent impedes the transmission of the fragrant vapors to the surrounding space, which leads to reduced effectiveness of the air freshening device.

It is accordingly an object of the present invention to provide a holder for an air freshener that overcomes the drawbacks of the devices of the known art.

SUMMARY OF THE INVENTION

In accordance with the inventive concept there is provided a holder for an air freshener having a wall section with a perimeter, a forward facing rim disposed along said perimeter, and a rearward facing rim disposed along said perimeter forming a rear space for containing the air freshener.

According to a further feature, the forward facing rim defines a forward facing image area on said wall section. According to another feature there is provided a holder wherein the rearward facing rim has cutouts for allowing air-freshening vapors from the air freshener to escape.

The image area may further include at least one picture aligned within the forward facing rim.

In the holder according to the invention at least part of the holder may be of structural foam wherein the foam is of an open-cell type having porosity allowing air-freshening vapors to migrate through the open cell foam.

According to an additional feature the rearward facing rim includes a hanger device for hanging the holder on a pin extending from a wall.

The holder according to the invention may include mounting means on the rear wall section, operative for mounting the air freshener in said rear space.

In the holder according to the invention, the perimeter can have a shape according to at least one of a circle, an oval, a rectangle, and a triangle.

According to still another feature of the holder, the forward facing rim has a cross-section composed of segments being formed as straight lines, curves, and circle sections, for decorative purposes.

The invention may also provide an air freshener assembly having an air freshener, a holder for the air freshener, the holder including a wall section having a perimeter, a forward facing rim disposed along said perimeter, a rearward facing rim disposed along the perimeter forming a rear space for containing the air freshener.

In the holder for an air freshener according to the invention, the image area contains an image of porous material adapted to admit through the image the fragrant vapors of said air freshener.

Other features which are considered as characteristic for the invention are set forth in the appended claims.

Although the invention is illustrated and described herein as embodied in a holder for an air freshener, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
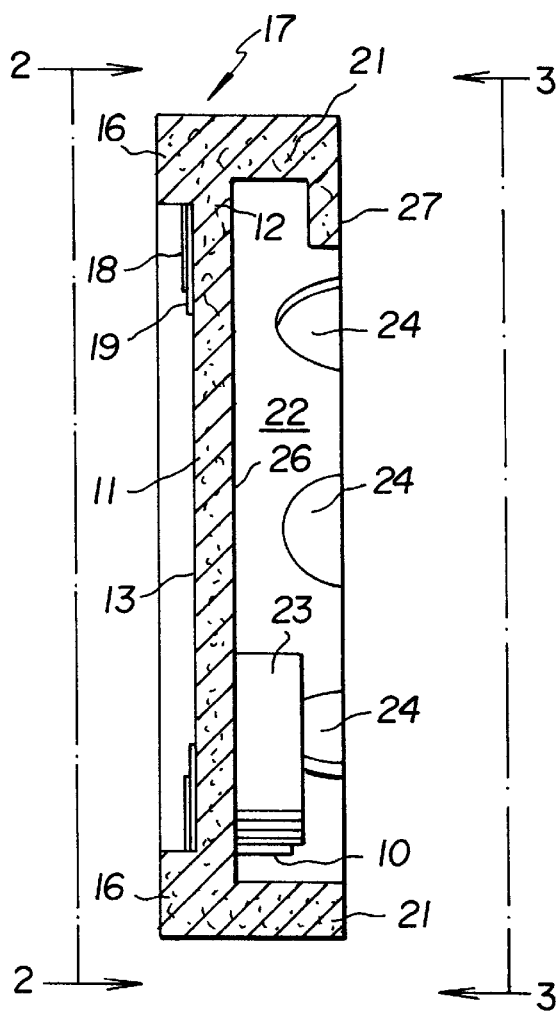
FIG. 1 is a cross-section of the invention showing its major components.
Figure 2:
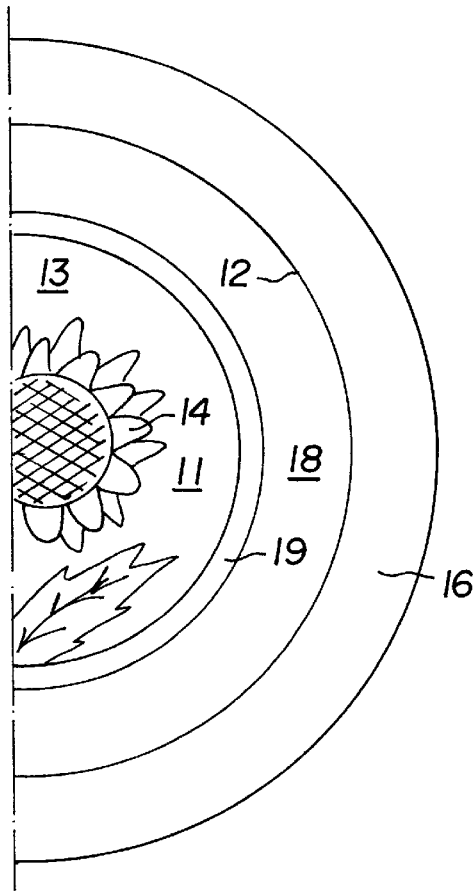
FIG. 2 is a fragmentary view of the invention seen along the line 2—2 of FIG. 1, showing part of the image area.

FIG. 1 is a cross-sectional side view of the invention showing a wall section 11 having a perimeter 12, and a forward facing image area 13 which is suitable for displaying an image or picture 14, seen partly in FIG. 2. The wall section 11 has along its perimeter 12 a forward facing rim 16 that projects from the image area 13 as a picture frame 17.

Figure 5:
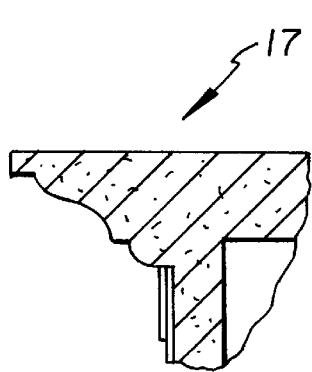
FIG. 5 is a cross-sectional fragmentary view of a section of the forward facing rim in a decorative shaping of the rim.

The picture frame 17 may have a decorative profile, for example as shown in the fragmentary view of FIG. 5, wherein the frame has a contour composed of curved and/or straight sections for enhanced appearance, similar to that of a conventional decorative picture frame.

The image area 14 may be enhanced by one or more perimeter picture mats 18, 19 as often provided on good quality picture frames.

Figure 6:
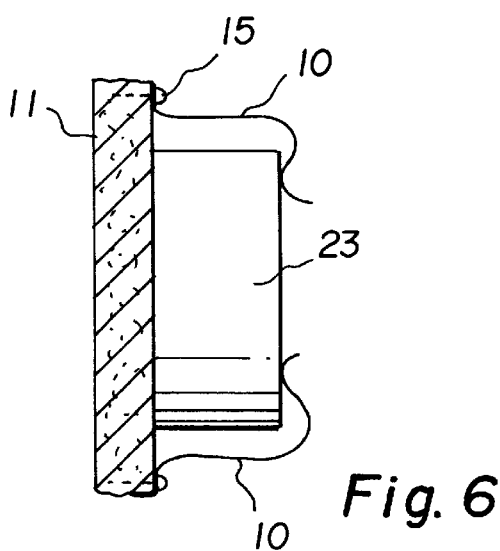
FIG. 6 shows a wall section and springs for holding the air freshener attached to the back side of the wall section.

A rearward facing rim 21 projects rearwardly from the wall section 11 forming therewith a rear space 22, which serves to contain the air freshener 23, retained by suitable means, such as protrusions 10a, to the back side of the wall section 11. The mounting means may also include e.g. hook-and pile fasteners (velcro®), flexible springs (FIG. 6), adhesive screws, snapfasteners or the like. FIG. 6 shows as an example spring holders 10 attached by screws or rivets 15 to the wall section 11, which serve to secure the air freshener 23 to the back side of wall section 11. A plurality of cutouts 24 are provided in the rearward facing rim 21 which enhance the transmission of fragrant vapors from the air freshener 23 to the adjacent environment.

FIG. 2 is a partial front view of the air freshener holder seen along the line 2—2 of FIG. 1: The holder elements described above are shown with the same reference numerals as in FIG. 1. A typical image 14 is shown applied to the forward facing side 13 of the wall section 11.

The entire holder is advantageously made of a structural porous foam of the type having an open cell composition, which allows the fragrant vapors from the air freshener to migrate through the various parts of the holder. A typical type of such foam is known as styrofoam, but several other types of rigid foam are well known. In order to facilitate migration of the fragrant vapors from the air freshener 23 through the wall section 11, the image 14 is advantageously also of an air permeable type, attained by for example screen-printing of the image on the wall section 11. Alternatively the image may be printed on a porous base material which is attached to the wall section 11 by suitable attaching means.

Figure 3:
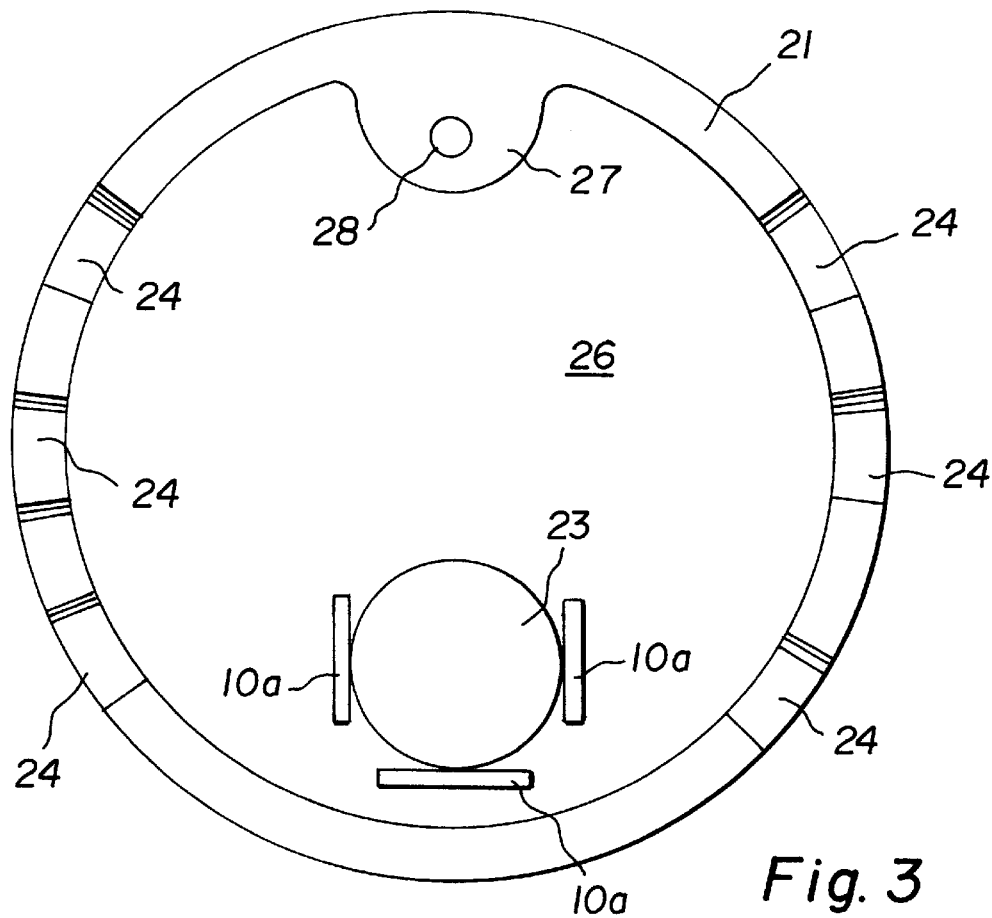
FIG. 3 is a rearward-facing view of the invention showing the air freshener mounted on the rearward facing wall section.

FIG. 3 is a rear view of the air freshener holder seen along the line 3—3 of FIG. 1, showing the rearward facing rim 21 with cutouts 24, and the air freshener 23 attached to the back side 26 of the wall section 11 by means of protrusions 10a. FIG. 3 also shows a hanger part 27 with a hole 28 for receiving a nail or pin extending from a wall to which the holder is attached.

Figure 4A:
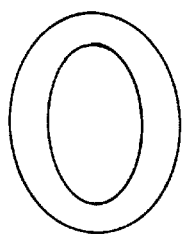
FIG. 4 shows examples of various shapes of the invention.
Figure 4B:
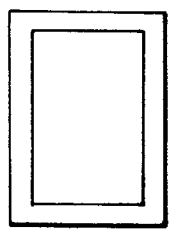
Figure 4C:
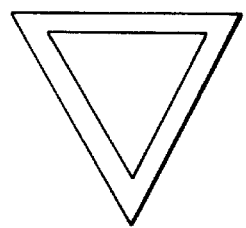

FIG. 4 shows various forms of the holder, other than the circular form described above. The holder may have the form of an oval, rectangle, or triangle shown respectively in detail figures (a), (b) and (c), but is not limited to just such forms.

I claim:

1. A holder for an air freshener comprising a wall section having a perimeter, a forward facing rim disposed along said perimeter, a rearward facing rim disposed along said perimeter forming a rear space for containing the air freshener, wherein at least part of said holder is made of structural foam of an open cell type.

2. A holder according to claim 1 wherein said forward facing rim defines a forward facing image area on said wall section.

3. A holder according to claim 1 wherein said rearward facing rim has cutouts for allowing air-freshening vapors from the air freshener to escape.

4. A holder according to claim 2 wherein said image area includes at least one picture mat aligned with said forward facing rim.

5. A holder according to claim 1, wherein said foam has a porosity allowing air-freshening vapors to migrate through the open cell-foam.

6. A holder according to claim 1 wherein said rearward facing rim includes an integral hanger part for hanging the holder on a pin extending from a wall.

7. A holder according to claim 1 including mounting means on said wall section operative for mounting the air freshener in said rear space.

8. A holder according to claim 1, wherein said perimeter has a shape according to at least one of a circle, an oval, a rectangle, and a triangle.

9. A holder according to claim 1, wherein said forward facing rim has a cross-section composed of segments being formed as straight lines, curves, and circle sections.

10. A holder for an air freshener according to claim 2, wherein said image area contains an image formed of porous material adapted to admit through the image the fragrant vapors of said air freshener.

11. A holder according to claim 1, wherein said foam does not include an added volatile fragrance.

12. A holder according to claim 1, further comprising a spring attached to said holder for holding the air freshener in said rear space.

13. An air freshener assembly comprising an air freshener, a holder for the air freshener, said holder including a wall section having a perimeter, a forward facing rim disposed along said perimeter, and a rearward facing rim disposed along said perimeter forming a rear space for containing said air freshener, wherein at least part of said holder is made of structural foam of an open cell type.

\* \* \* \* \*